United States Patent
Greer et al.

(10) Patent No.: US 6,192,750 B1
(45) Date of Patent: Feb. 27, 2001

(54) PROCESS SENSOR ASSEMBLY AND SENSOR MOUNT

(75) Inventors: David G. Greer, Cambridge; Bryan D. Greer, Andover; Richard G. LaBorde, Maple Grove, all of MN (US)

(73) Assignee: Agrichem, Inc., Ham Lake, MN (US)

( * ) Notice: Subject to any disclaimer, the term of this patent is extended or adjusted under 35 U.S.C. 154(b) by 0 days.

(21) Appl. No.: 09/236,410

(22) Filed: Jan. 25, 1999

Related U.S. Application Data

(60) Provisional application No. 60/112,079, filed on Dec. 14, 1998.

(51) Int. Cl.[7] .................................................. G01F 15/14
(52) U.S. Cl. ................................................................ 73/273
(58) Field of Search ....................... 73/273, 431, 865.5, 73/865.8, 866, 863.21, 863.22, 863.41, 863.42, 863.43

(56) References Cited

U.S. PATENT DOCUMENTS

| | | | |
|---|---|---|---|
| 3,674,087 | * 7/1972 | Ackerman et al. | 165/2 |
| 4,168,466 | 9/1979 | Boldt . | |
| 4,958,741 | 9/1990 | Johanson . | |
| 5,202,837 | * 4/1993 | Coe et al. | 364/475 |
| 5,332,307 | 7/1994 | Le Gigan . | |
| 5,361,945 | 11/1994 | Johanson . | |
| 5,363,708 | 11/1994 | Johnson . | |
| 5,500,083 | 3/1996 | Johanson . | |
| 6,029,506 | * 2/2000 | Dilger | 73/46 |

* cited by examiner

Primary Examiner—William Oen
(74) Attorney, Agent, or Firm—Burd, Bartz & Gutenkauf

(57) ABSTRACT

A sensor assembly includes a sensor housing or mounting apparatus for positioning in a free flowing stream of particulate matter in order to accomplish on-line measurement of a physical property of the material such as moisture content. The housing has an inlet nozzle, a mid-section or sensing chamber, and a discharge section. The inlet nozzle has flow deflector plates that intercept a sample of material from the process stream from a single plane and channel it to the sensing chamber. A sensor is embedded in the walls of the sensing chamber and positioned to sense the material property of the passing sample. A discharge nozzle extends from the sensing chamber and has a constricted discharge opening in order to regulate flow through the sensing chamber. The discharge nozzle has a pair of downwardly convergent deflector plates such that the flow of particulate matter is restricted in a single vertical plane that is perpendicular to the vertical plane referenced by the inlet section.

20 Claims, 3 Drawing Sheets

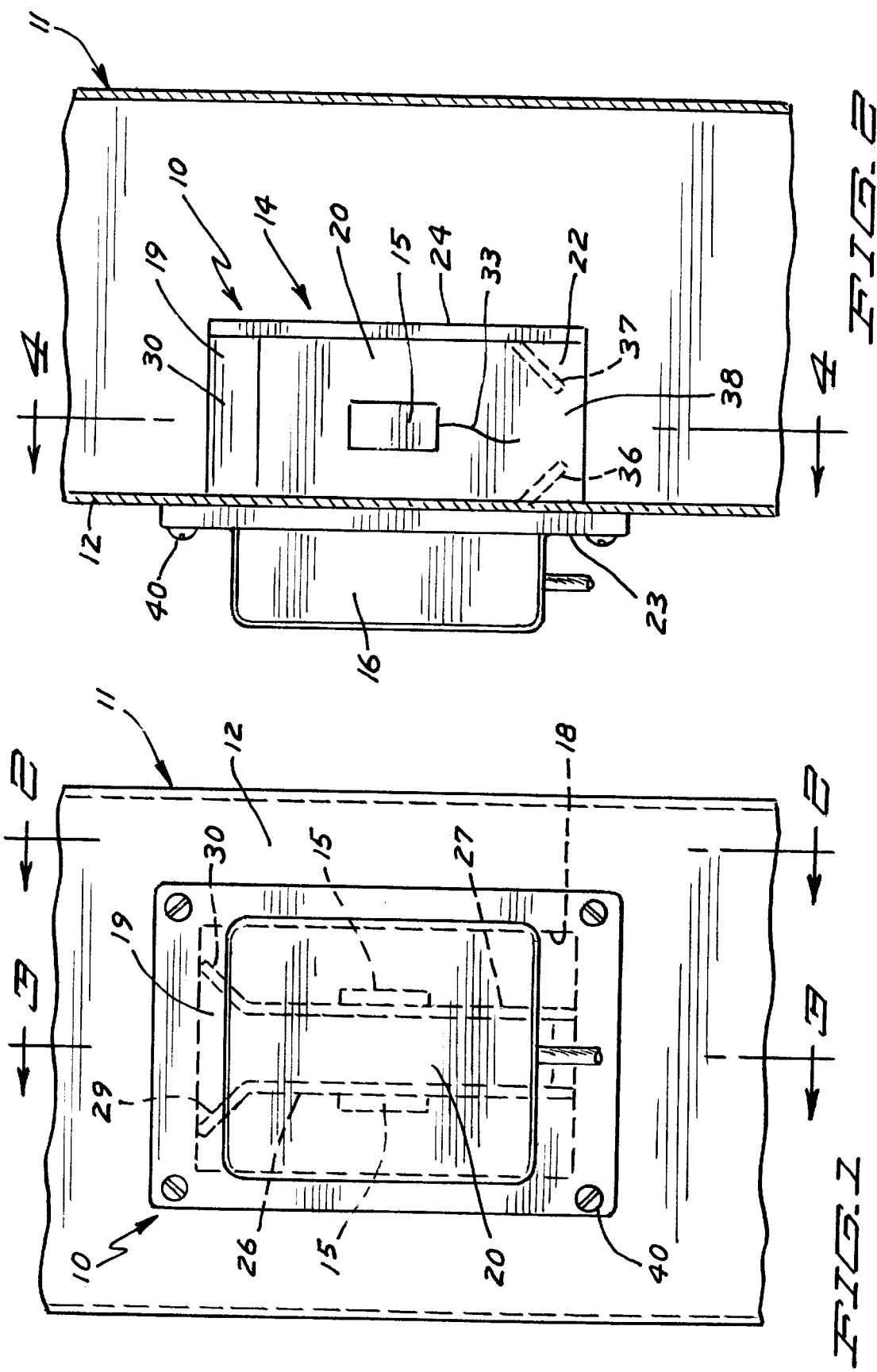

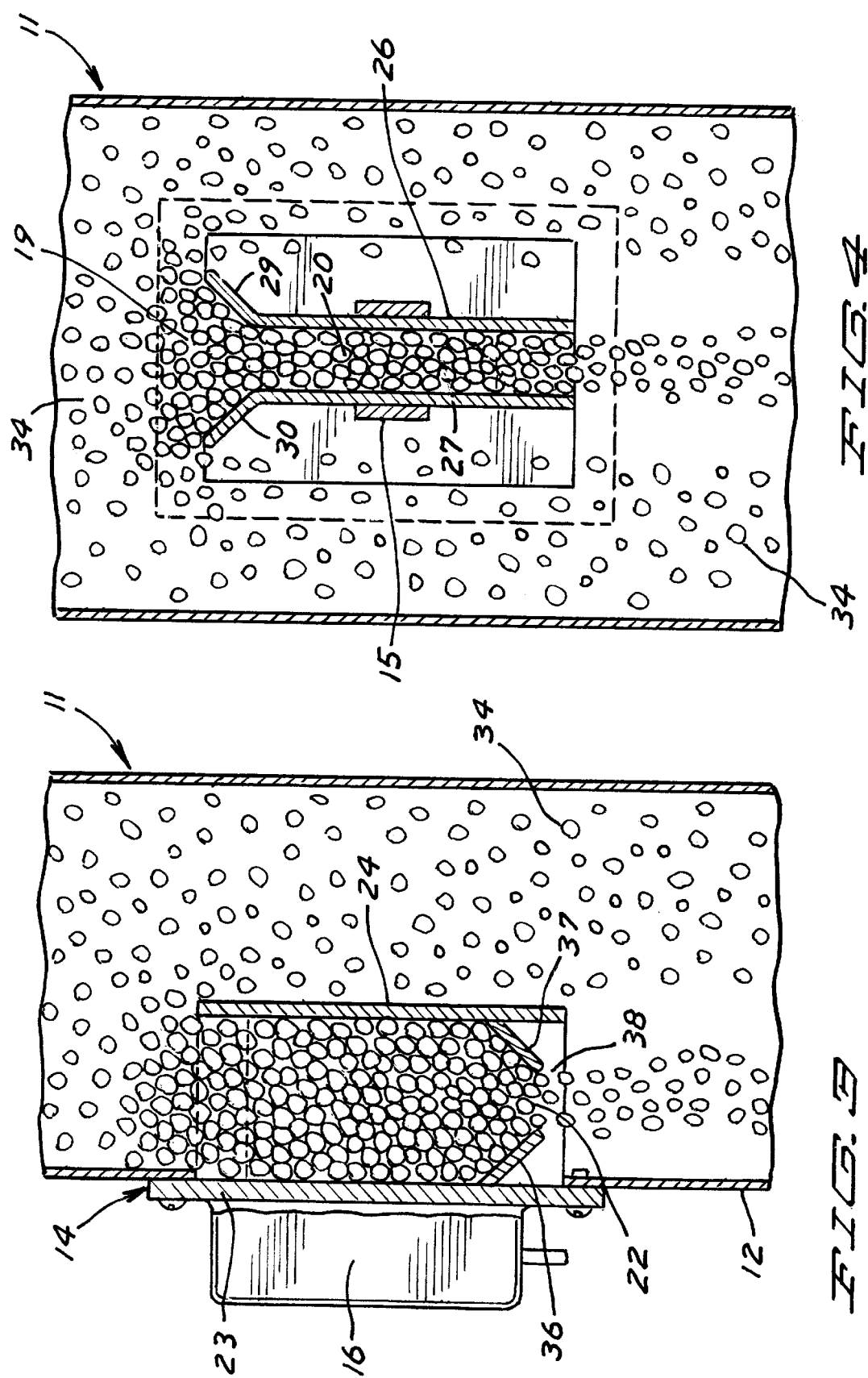

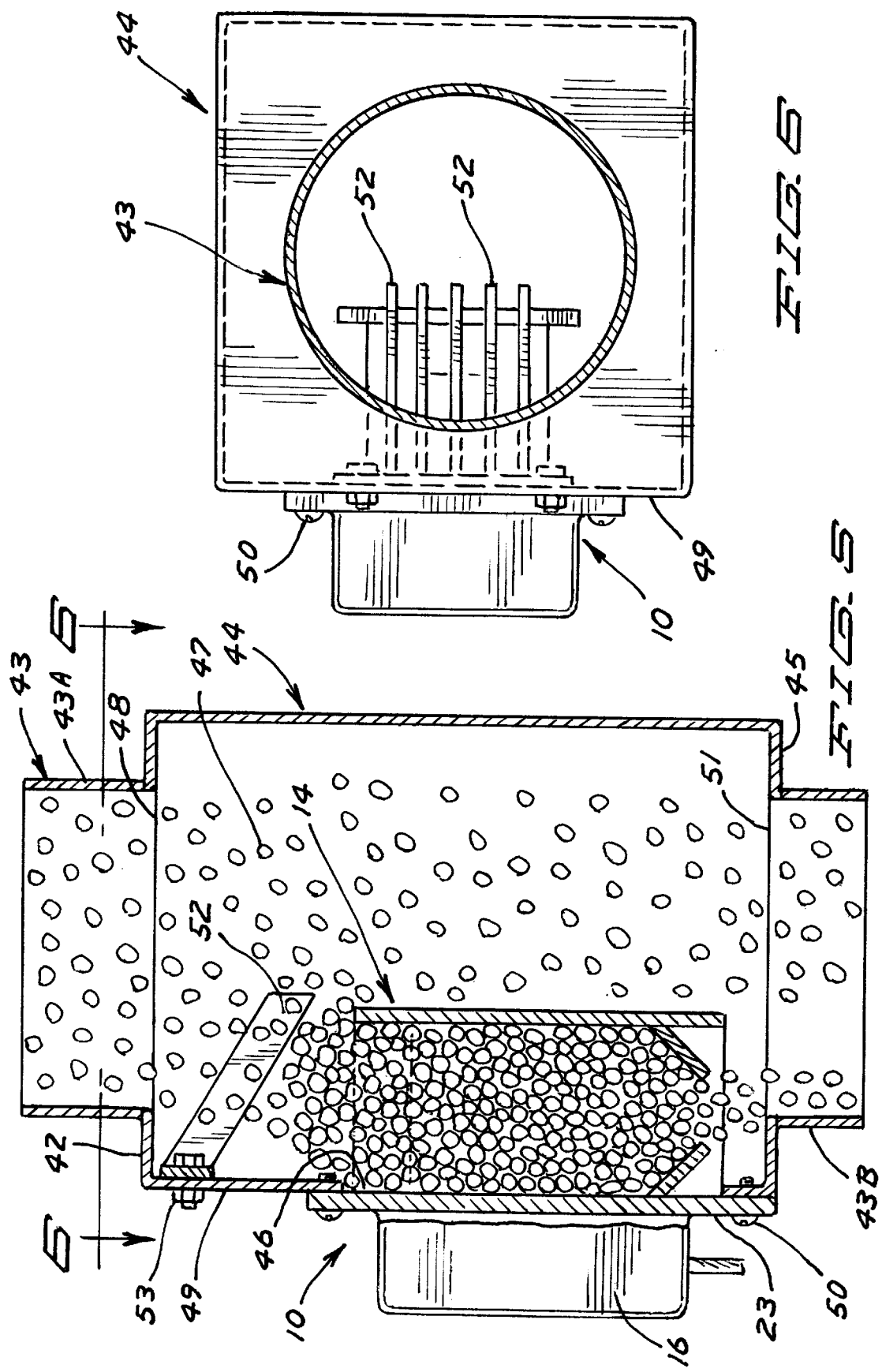

PROCESS SENSOR ASSEMBLY AND SENSOR MOUNT

This application claim benefit to Provisional Application Ser. No. 60/112,079 filed Dec. 14, 1998.

BACKGROUND OF THE INVENTION

Numerous manufacturing processes call for on-line monitoring of a physical property of a free flowing granular or particulate material. Examples of properties to be monitored are moisture content, temperature, color, etc. An example of a process where on-line monitoring is employed is manufacturing of feed. A difficulty is encountered in presenting to the on-line sensors a representative sample of the free flowing material in order that the on-line assay will be meaningful. That is, what is "seen" by the sensor must accurately represent the process stream. Physical characteristics of free flowing particulate materials compound the basic problems encountered when placing an on-line sensor in a process stream. Any attempt to divert or restrict the particulate flow invites plugging or bridging. This is particularly true of sampling devices employing a conical or pyramidal shape that abruptly restricts the particulate flow from all directions as it enters the inlet. Plugging or bridging stops flow through the sensing device. In addition, the flow pattern of the particulate material is seldom uniform. Augers, bucket elevators and such devices are commonly used to move the particulate material, giving the flow pattern a pulse. The particles comprising the stream are frequently of irregular shape and size.

SUMMARY OF THE INVENTION

The invention pertains to a sensor assembly and in particular a one-piece sensor mounting apparatus for measurement of a physical property of a free flowing material having a vertical flow component. The sensor mounting apparatus includes an open ended housing. The housing has an inlet section, a body having a sensing chamber, and a discharge section located vertically beneath the inlet. The inlet section includes an inlet nozzle shaped to be a single dimensional flow restrictor that collects a sample from the process stream in a single vertical plane and channels it to the throat of the sensing chamber. The inlet nozzle has opposite parallel vertical walls, and opposite downwardly convergent inclined walls that restrict flow from the one dimension. The sensing chamber has a central vertical passage for conveying the particulate sample past a sensing station. A sensor is connected to the walls of the sensing chamber in position to sense the material property of the passing sample. Since the particle sample flow is restricted in a single plane, the propensity to bridge or plug is lessened.

The discharge section of the sensor housing includes a discharge nozzle characterized by opposite parallel vertical walls, and opposite downwardly convergent inclined walls. The walls are positioned such that the particulate material is discharged from a single vertical plane that is perpendicular to the vertical plane referenced by the inlet section.

The configuration of the sensor housing produces a consistent uniform flow and density of a sample of particulate matter diverted from the process stream through the sensing chamber.

IN THE DRAWINGS

FIG. 1 is a front elevational view of a sensor assembly according to one form of the invention installed in a process stream duct;

FIG. 2 is a sectional view of the sensor assembly and duct of FIG. 1 taken along the line 2—2 thereof;

FIG. 3 is another sectional view of the sensor assembly and duct of FIG. 1 taken along the line 3—3 thereof and showing a stream of particulate matter flowing in the duct;

FIG. 4 is a sectional view of the sensor assembly and duct of FIG. 2 taken along the line 4—4 thereof;

FIG. 5 is a sectional view like that of FIG. 3 showing an alternative embodiment of sensor assembly according to the invention; and FIG. 6 is a sectional view of the sensor assembly and duct of FIG. 5 taken along the line 6—6 thereof with the particulate matter absent for purposes of illustration.

DESCRIPTION OF PREFERRED EMBODIMENTS

Referring to the drawings, there is shown in FIGS. 1 and 2 a sensor assembly according to the invention indicated generally at 10 installed in a duct 11. Duct 11 is part of a particulate matter conveying system whereby particulate matter moves through it under the influence of gravity. For example, duct 11 can carry a process stream in the form of grain as part of the manufacture of animal feed. Duct 11 is normally vertical but could be inclined with a vertical component.

Sensor assembly 10 is installed in an opening 18 in one wall 12 of duct 11. Sensor assembly 10 includes a sensor mount or open-ended housing 14 disposed about a generally vertical axis and carrying sensor elements 15. Housing 14 is mounted internally of duct 11 and is connected to an exteriorly mounted component cabinet 16 which can contain necessary electronic components attendant to the operation of sensor elements 15.

Housing 14 has an inlet section with an inlet nozzle 19, a mid-section or body having an axial passage or sensing chamber 20, and an outlet section with a discharge nozzle 22. Inlet nozzle 19 is trapezoidal in shape in order to intercept from a single plane a sample of particulate matter moving in the process stream of duct 11 and divert it to the sensing chamber 20. Sensing chamber 20 has a uniform cross sectional area for presentation of the particulate material sample to the property sensors 15. The discharge nozzle 22 restricts to the flow of material from the sensing chamber 20. Discharge nozzle 22 restricts the flow of particulate material in a single plane so as to avoid bridging and plugging.

Housing 14 has first and second or front and back vertical walls 23, 24. Third and fourth side walls 26, 27 connect to the front and back walls. In the preferred embodiment shown in FIGS. 1 through 4, the various vertical walls are connected in a rectangular or square configuration.

Inlet nozzle 19 includes top deflector plates or particulate flow deflectors 29, 30 connected to the upper edges of opposite sidewalls 26, 27 of housing 14. Flow deflectors 29, 30 are oppositely inclined and upwardly divergent. Nozzle 19 presents a single dimensional, upwardly open flow restricting device for collection of a particulate sample from a single vertical plane. The collection plane of nozzle 19 is parallel to FIGS. 1 and 4, and has a thickness equal to the width of the deflectors 29, 30.

Front and back walls 23, 24 are wider than the side walls 26, 27. The top vertical sections of the front and back walls 23, 24 abut the edges of the top deflectors 29, 30 and close the sides of inlet nozzle 19.

Sensing chamber 20 has a uniform cross-section between inlet nozzle 19 and discharge nozzle 22. Sensor elements 15 are located on the side walls 26, 27 of the housing 14 exterior to the sensing chamber 20. Sensors 15 measure a physical property of the passing particulate material. Examples of such process sensors are: a thermocouple for temperature determination; a near infrared sensor for moisture, protein or other assays of feedstuffs; any other reflectance spectroscopic sensor; capacitance plates for monitoring dielectric properties such as moisture content. The sensors are connected by a suitable means indicated at 33 in FIG. 2, to electronics contained in the cabinet 16 and thereafter to control or monitoring devices according to the particular application.

Discharge nozzle 22 includes a pair of bottom plates or flow deflectors 36, 37 disposed opposite one another and inclined so as to be downwardly convergent. Bottom deflectors 36, 37 are offset 90° from top deflectors 29, 30 about a vertical axis. The upper edges of the bottom deflectors plates are connected to the front and back housing walls 23, 24 beneath sensing chamber 20. Discharge nozzle 22 is defined by deflectors 36, 37 and the vertical housing walls 26, 27. Nozzle 22 terminates at a discharge opening 38. Material from the sensing chamber 20 is funneled by discharge nozzle 22 to the discharge opening 38. Discharge nozzle 22 presents an upwardly open single dimensional flow restricting device open to the sensing chamber 20. Nozzle 22 channels material from the sensing chamber 20 in a single vertical plane. The discharge plane of discharge nozzle 22 is parallel to the plane of FIGS. 2 and 3 and perpendicular to the inlet or collection plane of inlet nozzle 19. The discharge plane of discharge nozzle 22 has a thickness equal to the width of the deflectors 36, 37. The flow of material from the sensing chamber 20 to the discharge opening 38 is restricted in a single plane, that of discharge nozzle 22. Such one dimensional restriction decreases the tendency of the material to bridge or plug.

Sensor 10 is installed in the opening 18 of wall 12 of duct 11. Front wall 23 of housing 14 has sufficient dimensions to overlap the edges of opening 18 and function as a mounting plate. Bolts or clamps 40 fasten the front wall 23 to the exterior surface to the duct wall 12 with housing 14 positioned interiorly of the duct 11 as shown.

Operation of the sensor assembly 10 can be seen with reference to FIGS. 3 and 4. A process stream 34 of particulate material is passing downwardly through the duct 11 under the influence of gravity. The inlet nozzle 19 presents an upwardly open mouth for receipt of a sample of particulate matter drawn from the passing stream. The sample is drawn from a single plane that is parallel to FIG. 4.

The particulate material is channeled through the sensing chamber 20. The single dimensional restriction of the flow of the particular matter lessens the propensity to bridge or plug at the inlet throat. Particulate matter passes through housing 14 and discharges through exit opening 38 of discharge nozzle 22. Exit opening 38 has a cross section area less than that of the sensing chamber. Under normal use, the housing 14 is continuously full whereby there is a uniform continuous flow of particular matter past the sensors. Discharge nozzle 22 restricts flow through the sensing chamber. A pool of particulate matter collects in the inlet nozzle 19 above the sensing chamber. This forms a "pillow" of particulate matter that creates reproducible density or packing in the cell. Excess particulate material flows over the sides of the housing. The constant column standardizes the pressure and density in the sensing chamber to create a consistent, dynamic sample for assay in the sensing chamber. The pillow of particulate material serves as a shock absorber and pulse dempener, protecting the sensing cell from continuous impact from the material and irregular flow patterns. The contact between the sensing cell and the material is reduced to a regulated sliding instead of a continuous pounding.

As shown, sensor assembly 10 has a vertical axis as does duct 11. The sensor assembly and duct can be inclined while having a generally vertical axis or an axis with a major vertical component. Such inclination should preferably not exceed 45°.

It is important that the sensor housing be installed in a manner that will permit it to intercept the particulate stream and withdraw a representative sample while allowing the excess material to freely bypass. In certain instances a chute or downspout will not furnish sufficient space for installation of the sensor housing and still allow relatively unencumbered bypass of excess material. FIGS. 5 and 6 illustrate an alternative embodiment of the invention to overcome this problem. FIGS. 5 and 6 show an undersize chute or downspout 43 carrying a free flowing stream of particulate material 47. The transverse dimension of downspout 43 is insufficient to permit normal installation of the sensor assembly 10. Accordingly, a mounting box 44 of sufficient size to mount the sensor housing is installed intermediately in the duct 43. Box 44 has a top wall 42 with an opening 48 coextensive with the perimeter of an upper section of the duct 43A. Box 44 has a bottom wall 45 with an opening 51 also coextensive with the perimeter of the opening of an adjacent lower section of duct 43B. Box 44 has a front wall 49 with a front opening 46. The sensor assembly 10 is like that described with reference to FIGS. 1–4. The sensor assembly 10 is installed in the opening 46 with bolts or clamps 50 passing through the front wall 23 and adjacent portions of the front wall 49 of box 44 surrounding the opening 46.

A scalper bar assembly is installed over the inlet to the sensor housing, and includes a plurality of parallel, spaced apart scalper bars 52 angularly mounted over the inlet inside of the box 44. Scalper bars 52 serve to deflect large foreign matter in the process stream from entering the sensor housing.

The interior dimensions of the box 44 are greater then those of the duct 43 whereby the sensor assembly 10 is conveniently installed therein. Box 44 provides a sufficient passageway for the particulate stream 47 past the sensor housing 14 while permitting an ample portion of the particulate stream to be diverted through the sensor housing. The box 44 is spacious enough to provide easy access to the sensor housing for observation, service and the like. The sensor housing is easily positioned with respect to the stream of particulate matter in order to intercept a representative sample. The box 44 presents a simple, low-cost solution to the problem of having a chute or down spout that is too narrow to permit conventional installation of the sensor assembly 10.

While there have been shown and described certain preferred embodiments of a sensor assembly according to the invention, it will be apparent that certain deviations and modifications can be had without departing from the scope and spirit of the invention.

We claim:

1. A process sensor assembly for measuring a physical property of a free-flowing vertical process stream of particulate material having a vertical component, comprising:

an open-ended sensor housing disposed about a generally vertical axis and having an open vertical passage for passage of particulate material and defining a sensing chamber;

an inlet nozzle connected to the top of the housing and comprising a single dimensional upwardly open flow restricting device to intercept a sample of passing particulate material from the process stream from a single vertical collection plane and divert it to the sensing chamber;

a discharge nozzle connected to the lower end of the housing having a discharge opening for discharge of particulate material from the housing, said discharge nozzle comprising a single dimensional upwardly open flow restricting device to restrict flow of particulate material in a single vertical discharge plane, said discharge nozzle positioned at 90° to the inlet nozzle so that the discharge plane is perpendicular to the collection plane referenced by the inlet nozzle; and process sensor means connected to the housing to detect a material property of the particulate material passing through the sensing chamber.

2. The process sensor assembly of claim 1 wherein:

the inlet nozzle has first and second top flow deflectors that are upwardly divergent from one another in order to collect said sample of particulate material from the process stream; and the discharge nozzle has first and second bottom flow deflectors opposite one another and downwardly convergent to the discharge opening.

3. The process sensor assembly of claim 2 wherein:

said housing has first and second opposite and parallel vertical walls, and third and fourth opposite and parallel vertical walls connected to the first and second walls in perpendicular relationship, defining said sensing chamber with said passage having a uniform cross-section.

4. The process sensor assembly of claim 3 wherein:

said top deflectors are connected to the upper edges of the third and fourth vertical walls and are upwardly and outwardly inclined therefrom forming said inlet nozzle.

5. The process sensor assembly of claim 4 wherein:

said bottom deflectors are connected to the first and second vertical walls of the housing opposite one another and are downwardly and inwardly extended therefrom to the discharge opening.

6. The process sensor assembly of claim 5 wherein:

the upper portions of the first and second walls of the housing form vertical sides of the inlet nozzle.

7. The process sensor assembly of claim 6 wherein:

the first and second walls are wider than the third and fourth walls of the housing, and the upper portions of the first and second walls form vertical sides for the inlet nozzle.

8. The process sensor assembly of claim 7 wherein:

said first wall of the housing is also a mounting plate for the sensor assembly;

an electronics cabinet connected to the first wall on the side opposite the other walls.

9. The process sensor of claim 8 including:

a mounting box having vertical side walls and top and bottom openings for installation of the mounting box on a vertical process stream duct that is undersize for installation of the process sensor housing;

one of the side walls of the mounting box having a mounting opening;

said process sensor housing installed in the mounting opening of the box with the first wall of the housing attached to said wall of the mounting box with the remaining walls of the housing inside the mounting box and the electronics cabinet outside of it.

10. A process sensor mount for placement in a free flowing stream of particulate material, comprising:

an open-ended housing disposed about a generally vertical axis having an open passage for passage of particulate material and defining a sensing chamber;

an inlet nozzle connected to the upper end of the housing and comprising an upwardly open single dimension restriction device to intercept particulate matter from a single vertical plane and channel it to the sensing chamber;

a discharge nozzle connected to the lower end of the housing and comprising an upwardly open single dimension restriction device orientated 90° from the device of the inlet nozzle, to restrict flow of particulate material from the sensing chamber in a single vertical plane that is perpendicular to the vertical plane referenced by the inlet nozzle;

said discharge nozzle having a discharge opening for discharge of particulate material from the housing.

11. The sensor mount of claim 10 wherein:

the inlet nozzle has first and second top flow deflectors that are upwardly divergent from one another in order to intercept said sample of particulate material from the process stream; and the discharge nozzle has first and second bottom flow deflectors opposite one another and downwardly convergent to the discharge opening.

12. The sensor mount of claim 11 wherein:

said housing has first and second opposite and parallel vertical walls, and third and fourth opposite and parallel vertical walls connected to the first and second walls in perpendicular relationship, defining said sensing chamber with said vertical passage having a uniform cross-section.

13. The sensor mount of claim 12 wherein:

said top flow deflectors are connected to the third and fourth vertical walls and are upwardly and outwardly inclined therefrom forming said inlet nozzle.

14. The sensor mount of claim 13 wherein:

said bottom flow deflectors are connected to the first and second vertical walls of the housing opposite one another and are downwardly and inwardly extended therefrom to the discharge opening.

15. The sensor mount of claim 14 wherein:

the upper portions of the first and second walls of the housing form vertical sides of the inlet nozzle.

16. A process sensor assembly for installation in a duct containing a free-flowing stream of particulate material comprising:

an open-ended sensor housing having first and second opposite and parallel walls, and third and fourth opposite and parallel vertical walls in perpendicular relationship to the first and second walls, defining a vertical passage and a sensing chamber having a uniform cross-section;

an inlet nozzle connected to the top of the housing comprising a single dimensional upwardly open restriction device to intercept a sample of passing particulate material from the process stream from a single vertical collection plane and channel it through the sensing chamber, said inlet nozzle including first and second opposite top flow deflectors that are connected to the upper edges of the third and fourth housing walls and are upwardly divergent from one another in order to collect said sample of particulate material from the vertical collection plane;

said housing having a discharge opening from the sensing chamber; and process sensor means connected to the housing to detect a material property of the particulate material passing through the sensing chamber.

17. The process sensor of claim 16 wherein:

the upper portions of the first and second walls of the housing form vertical sides of the inlet nozzle.

18. In the process sensor of claim 16 wherein:

the first and second walls of the housing are wider than the third and fourth walls of the housing, and the upper portions of the first and second walls form vertical sides for the inlet nozzle.

19. The process sensor assembly of claim 18 wherein:

said first wall of the housing is also a mounting plate for the sensor assembly;

an electronics cabinet connected to the first wall on the side opposite the other walls.

20. The process sensor assembly of claim 16 including:

a discharge nozzle connected to the lower end of the housing.

* * * * *